(12) United States Patent
Ollivier

(10) Patent No.: US 8,417,332 B2
(45) Date of Patent: Apr. 9, 2013

(54) ENDOCARDIAL STIMULATION/DEFIBRILLATION SYSTEM OF THE LEFT VENTRICLE

(75) Inventor: Jean-Francois Ollivier, Villiers-le-Bacle (FR)

(73) Assignee: Sorin CRM S.A.S., Clamart Cedex (FR)

( * ) Notice: Subject to any disclaimer, the term of this patent is extended or adjusted under 35 U.S.C. 154(b) by 160 days.

(21) Appl. No.: 13/101,508

(22) Filed: May 5, 2011

(65) Prior Publication Data

US 2012/0271369 A1    Oct. 25, 2012

(30) Foreign Application Priority Data

May 5, 2010    (FR) ...................................... 10 53499

(51) Int. Cl.
*A61N 1/00* (2006.01)
(52) U.S. Cl.
USPC .............................................. 607/5; 607/123
(58) Field of Classification Search ................ 607/4–28, 607/122, 123, 115, 116
See application file for complete search history.

(56) References Cited

U.S. PATENT DOCUMENTS

| 5,370,684 | A | 12/1994 | Vallana et al. |
| 5,378,247 | A | 1/1995 | Sasaki et al. |
| 5,728,140 | A | 3/1998 | Salo et al. |
| 6,385,492 | B1 | 5/2002 | Ollivier et al. |
| 7,620,457 | B2 | 11/2009 | Ollivier et al. |
| 2010/0010607 | A1 | 1/2010 | Doerr |
| 2010/0069983 | A1 | 3/2010 | Peacock, III et al. |

FOREIGN PATENT DOCUMENTS

| DE | 102008040304 | 1/2010 |
| EP | 0993840 | 4/2000 |
| EP | 1516644 | 3/2005 |
| EP | 2143464 | 1/2010 |
| WO | WO 2008058265 | 5/2008 |

OTHER PUBLICATIONS

Foreign Search Report (Annexe Au Rapport De Recherche Preliminaire Relatif A La Demande De Brevet Francais No. FR1053499 FA737125), Dec. 8, 2010.

*Primary Examiner* — Scott Getzow
(74) *Attorney, Agent, or Firm* — Foley & Lardner LLP

(57) ABSTRACT

A system for the endocardial stimulation/defibrillation of the left ventricle. This system includes a generator (60) and an endocardial lead. The lead includes a lead body (26) whose distal end (30) extends into the right ventricle (14) and is provided with a mechanism to anchor (32) the distal end to the interventricular septum (20). The lead body carries on it a stimulating and/or defibrillation electrode (38) (64, 66). A microcable (42) extends into the lead body and beyond, with an intermediate portion (56) crossing from one side of the interventricular septum (20) to the other, and an active free portion (58) that emerges in the left ventricle (16). The microcable is coupled to the generator, to produce an electric field (62) between, on one hand, the stimulation electrode (38) or defibrillation electrode (64, 66) of the lead body and, on the other hand, a bare region of the active free portion (58) of microcable (42).

19 Claims, 4 Drawing Sheets

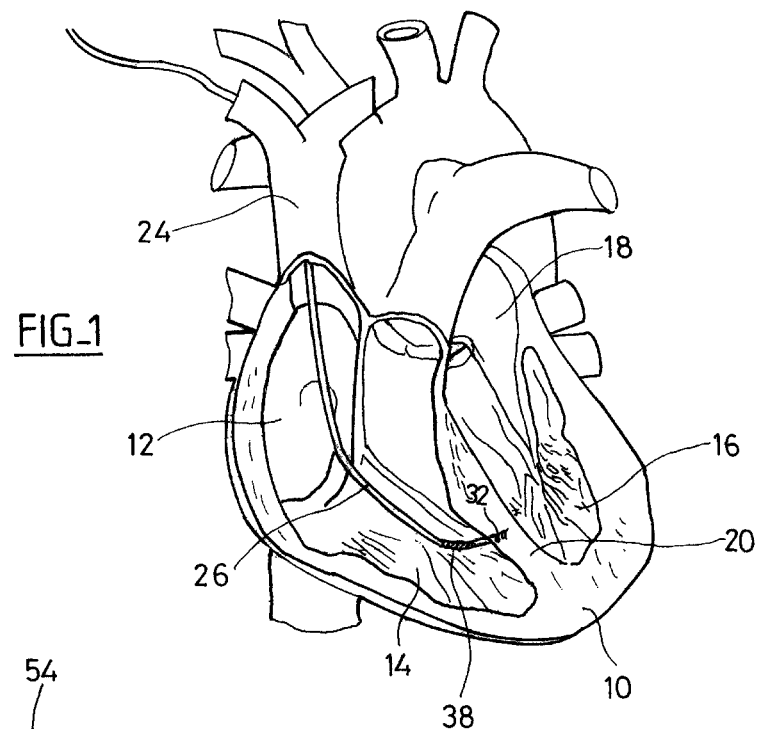
FIG_1
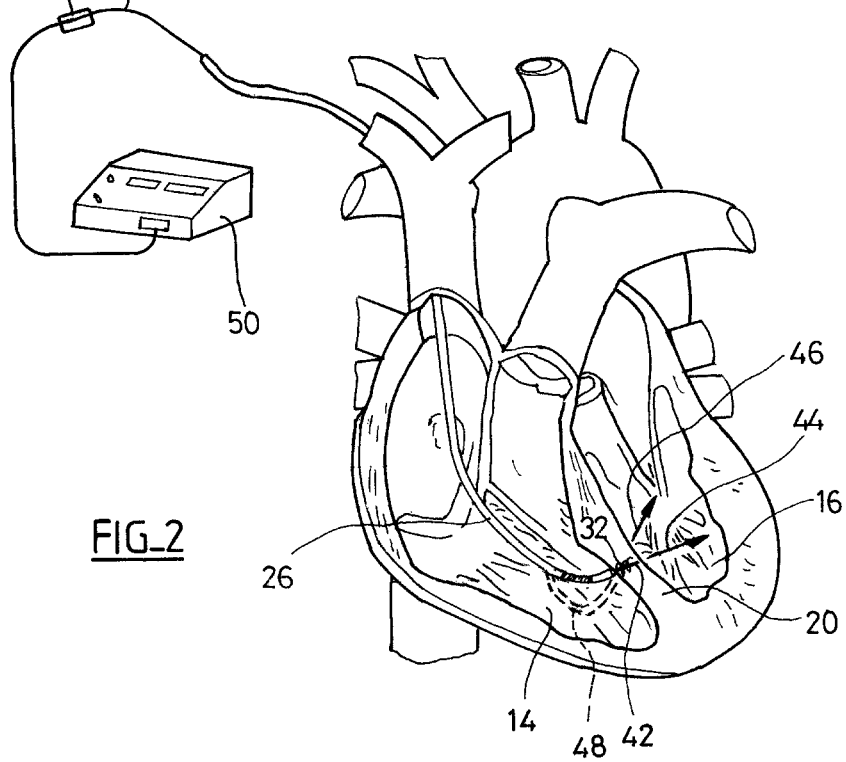
FIG_2

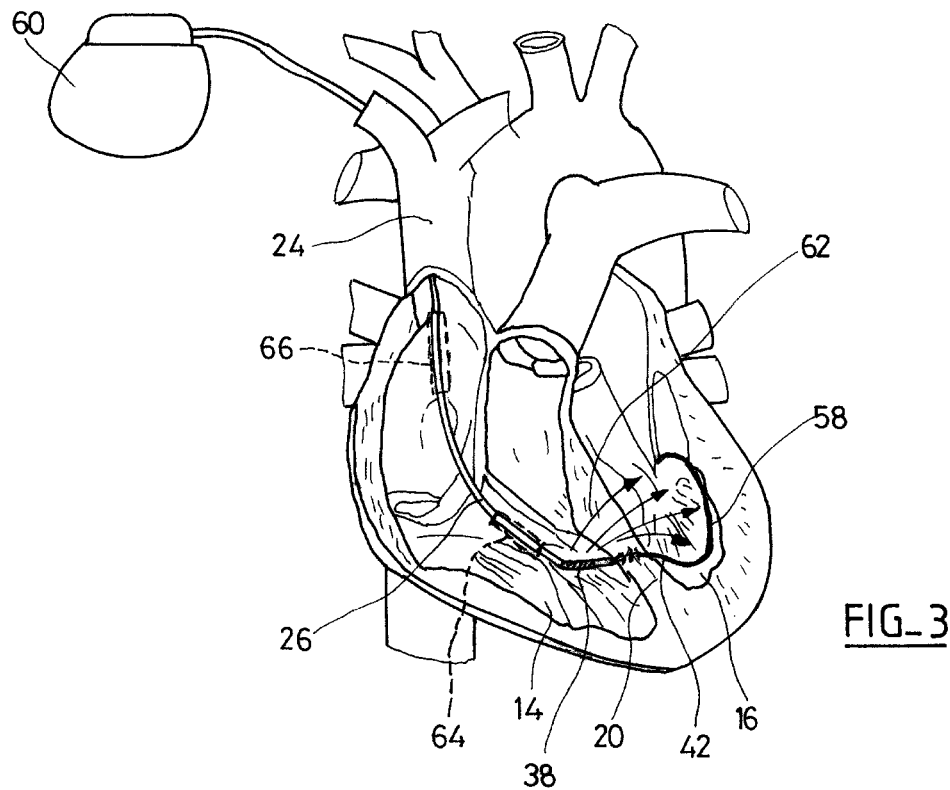
FIG_3
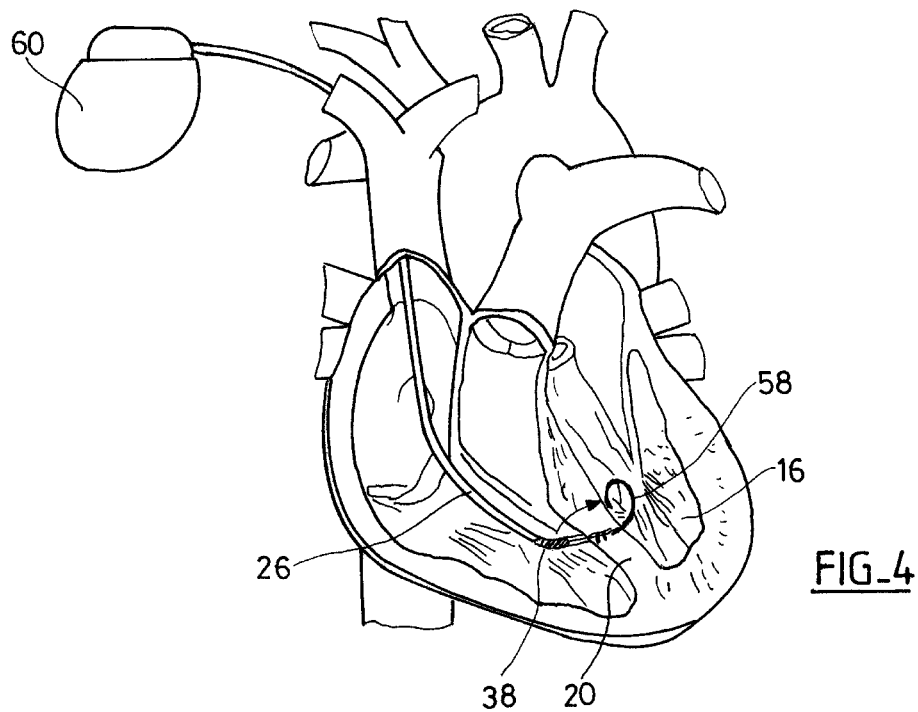
FIG_4

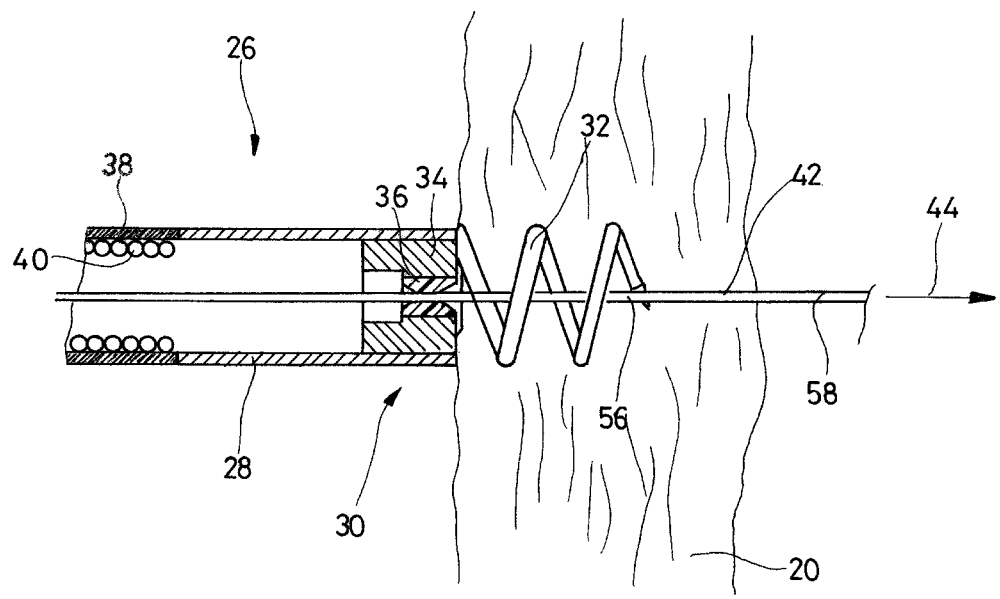
FIG_5
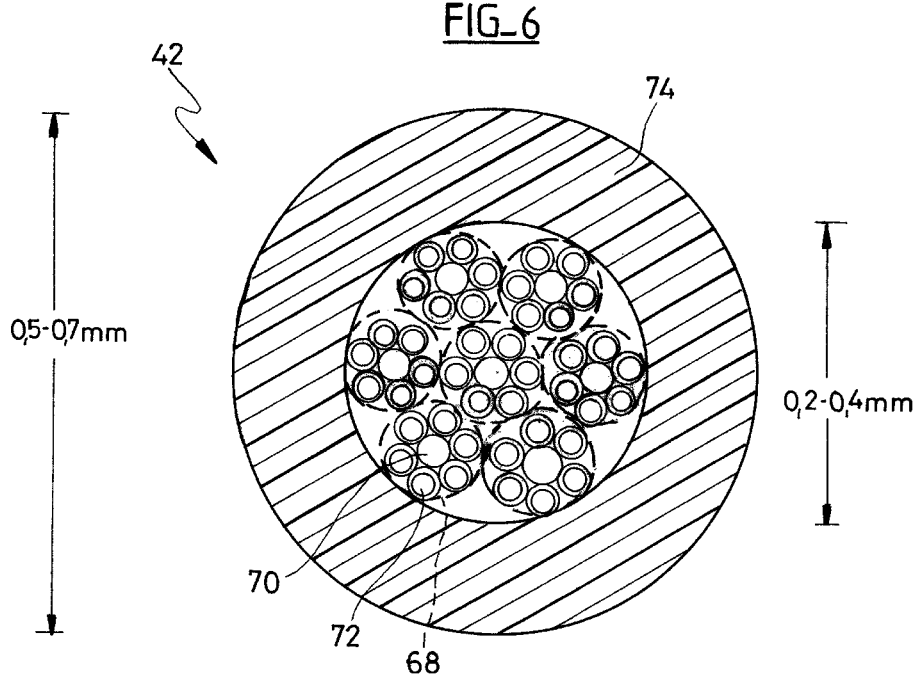
FIG_6

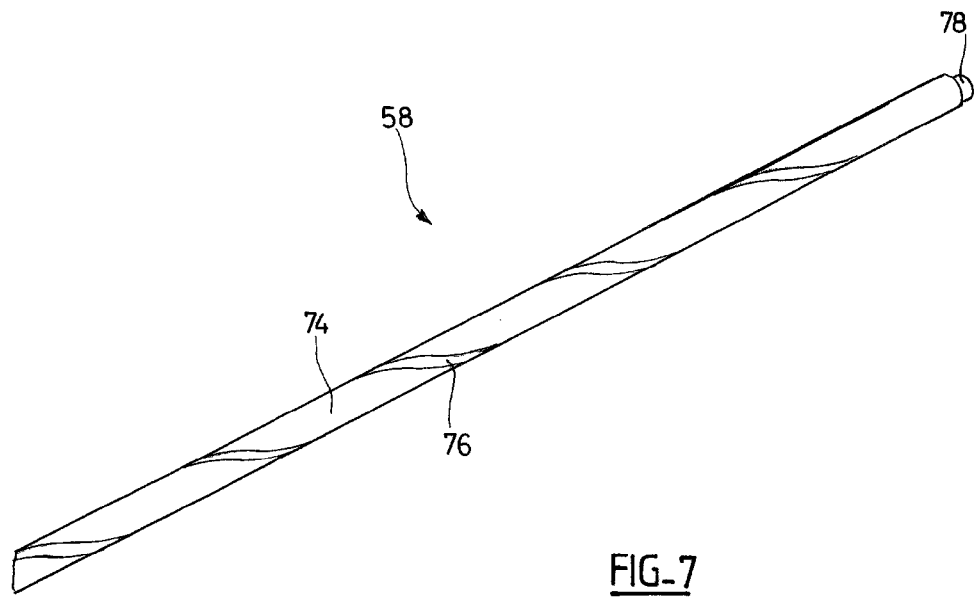
FIG_7
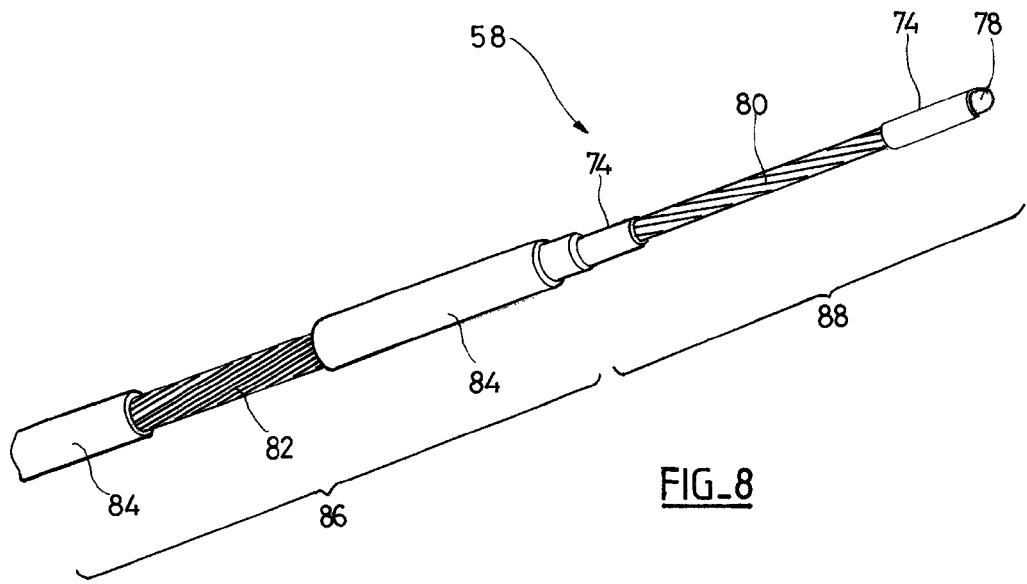
FIG_8

ENDOCARDIAL STIMULATION/DEFIBRILLATION SYSTEM OF THE LEFT VENTRICLE

The present application claims the benefit of French application Ser. No. 10/53499 entitled "Endocardial Stimulation/Defibrillation System of the Left Ventricle" and filed May 5, 2010, which is hereby incorporated by reference in its entirety.

FIELD

The present invention relates to "active implantable medical devices" as defined by the 20 Jun. 1990 Directive 90/385/EEC of the Council of the European Communities, particularly to devices that continuously monitor heart rhythm and deliver, if necessary, at the heart electrical pulses for stimulation, defibrillation or resynchronization, and more particularly to stimulation of the left ventricle on an endocardial site, by direct application of stimulation pulses to the inner wall of the left ventricle.

BACKGROUND

For stimulation of the right ventricle, the implantation of a lead through the right peripheral venous network typically suffices. However, to stimulate the left ventricle, the situation is more complex and the solution most often adopted is to introduce a lead into the coronary system via the right atrium and the coronary sinus ostium. Such a lead—which can be described as an endocardiac lead, but not as an endocardial lead—is described, e.g., in EP 0993840 A1 and its counterpart U.S. Pat. No. 6,385,492 (both assigned to Sorin CRM S.A.S., previously known as ELA Medical), and in the commercial product marketed under the name Situs LV by Sorin CRM, Clamart, France.

This implantation technique is not always feasible, however, especially when the conformation of the coronary sinus is too rugged, or when the patient has too much thrombosis. Indeed, the precise positioning of the electrode or electrodes to stimulate the left ventricle through the myocardium wall is a critical parameter, and it is not always possible to obtain a satisfactory configuration of the stimulation site.

Another known technique is to stimulate the left ventricle by applying stimulation pulses to the ventricular septum wall (also known as the interventricular septum), using a lead introduced into the right ventricle. One such stimulation technique of the left ventricle by a lead introduced into the right ventricle is described, e.g., in EP 1428550 A1 (De Bellis/P.A. SpA & M).

The U.S. Pat. No. 5,728,140 A also discloses a technique of left ventricular transeptal stimulation, without introduction of an electrode into the left cavity. Specifically, this device includes implanting a screw electrode penetrating the right septum wall, but whose length is slightly less than the thickness of the wall at the location of the stimulation site, so that the end of the screw approaches the left septal wall without crossing it.

If it is desirable to stimulate directly the left ventricle by an endocardial approach, the only techniques proposed so far are to drill a hole in the interatrial or interventricular septum, and then to introduce a lead through the septum until it comes into contact with a point of the left ventricle wall, where it is then anchored (e.g., by a fixation screw). The pacing pulses are applied directly to this selected endocardial site in the left ventricle.

This procedure, as currently implemented, however, has high operative risks, including risks of accidental perforation of the aorta, or dissection of the walls of the right atrium by a sudden rotational movement of the needle used for piercing the septum. Another risk of this technique is that of an air embolism, because the opening element in the left ventricle is a hollow catheter. To avoid this risk, it is imperative to take many precautions when handling hemostatic valves, to comply with procedures for purging the equipment, etc. However, given the highly invasive nature of this procedure, uncertainties remain about the behavior in the long term in the arterial circulation, which involves anticoagulation medication to prevent postoperatively thromboembolism. Finally, this technique virtually excludes any subsequent extraction of the lead, given the excessive risks that would be incurred at the crossing of the septum.

In any event, this technique is very difficult to implement and requires great skill of the practitioner who must, in order to cross the septum, always ensure perfect positioning of the needle for piercing on the wall of the septum, the crossing of the septum having to be undertaken only if there is no doubt about the position of the needle. Specific drilling kits also have been developed for this purpose, such as that described in EP 1516644 A1 and its counterpart U.S. Pat. No. 7,620,457 (both assigned to Sorin CRM S.A.S., previously known as ELA Medical).

The disadvantages mentioned above are also found in the system as is described in WO 2008/058265 A2. This document proposes to use as "left ventricular electrode" an element, introduced into a screw catheter, comprising a pointed end and provided with a harpoon-shaped tip designed to provide an anchoring point in the left wall cavity. This electrode is activated by a pusher introduced into the catheter, so as to push the tip through the septum and then deploy the electrode in the left ventricle. The catheter is then screwed to the wall of the septum, on the right side.

The assembly described in this document requires very difficult maneuvers for implantation, very different from what practitioners are used to. Its use is also very traumatic to the tissues, for the septum as well as for the left ventricular cavity, given the necessarily large diameter of the three elements telescopically nested into each other (catheter, deployable electrode and pusher). The implantation is of course not reversible, due to the harpoon-shaped tip and to the large diameter of the hole made in the septum, which could not close naturally in case of withdrawal. In addition, the surface area of the stimulation is relatively high, which leads to poor electrical performances and to high power consumption.

OBJECT AND SUMMARY

It is therefore an object of the present invention to propose a left ventricular endocardial stimulation system involving implantation of a lead directly into the left ventricular cavity after passing through the septum—but which is much less invasive and overcomes the many disadvantages of the known techniques mentioned above.

Broadly, the present invention lies in the discovery that the known techniques require a puncture in the septal wall that has a diameter sufficient to introduce a guide catheter. The guide catheter is intended to establish a communication between the right and left ventricles through the septal wall, so that the left endocardial pacing lead can then be introduced.

The inventor has discovered that instead of a guide catheter associated with a lead crossing through the septum, the present invention provides a novel system including a conventional lead screwed onto the wall of the right ventricle in the septum, modified to have a partially isolated transeptal microcable that is extended out through this lead into the left ventricle until it comes into contact against a target site located in the left ventricle, for example, against the free wall of the left ventricle.

In one embodiment, the present invention is a system of the general known type disclosed in WO 2008/058265 A2, including: a housing for an implantable device such as a pacemaker, defibrillator and/or resynchronizer comprising a generator means for delivering electrical stimulation/defibrillation pulses between two terminals; and an endocardial lead comprising at least one distal stimulation/defibrillation electrode coupled on its proximal side to a corresponding one of the two terminals of the generator means.

The lead preferably includes a lead body made of a deformable material with an open inner lumen at its distal end, the distal end of the lead body extending into the cavity of the right ventricle and being provided with means for anchoring the lead to the interventricular septum wall, the lead body also comprising at least one stimulation/defibrillation electrode coupled on its proximal side to a first of the two terminals of the generator means.

The lead also includes: at least one structure that is deployable in the left ventricular cavity, comprising an electrically conductive body protected by an insulating sheath, this structure being housed and sliding in the lumen of the lead body, extending the entire length of the lead body and extendable beyond the distal end thereof. The part of the structure located beyond the distal end of the lead body comprises successively: a middle portion for crossing from one side of the interventricular septum wall to the other, and a free active part for emerging in the cavity of the left ventricle. The free part comprises at least one bare region. The structure is electrically coupled at its proximal end to the second of two terminals of the generator means, so as to produce upon activation of the generator means an electrical field between, on one hand, the stimulation/defibrillation electrode(s) of the lead body, and, on the other hand, the bare region of the active free part of the microcable. It should be understood that reference to the bare region is to an exposed (uninsulated) electrically conductive element.

In a preferred embodiment, the structure to be deployed in the cavity of the left ventricle is a microcable having an electrically conductive inner diameter, at least in the active free part, of between 0.2 and 0.4 mm. This embodiment of a microcable includes a strand formed from a plurality of strands with at least one strand comprising a first composite material with properties of mechanical resistance to bending fatigue greater than those of the other materials of the strand, and a second material that is a radioopaque material.

In a preferred embodiment, the length of the active free part is selected from between 30 and 120 mm, more preferably from 45 to 55 mm, and the length of the intermediate portion is selected from between 10 and 20 mm. Preferably, the diameter of the insulating sheath of the microcable is between 0.5 and 0.7 mm. In one embodiment, the at least one composite strand further comprises a third material having electrical conductivity properties superior to those of the other materials of the strand. In another embodiment, the microcable strand is formed of a plurality of composite strands, having a core wire comprising said second material that is radioopaque, the core wire being surrounded by composite wires each comprising said first material as a surface material.

In yet another embodiment, the free part of the active microcable includes a plurality of separate successive bare regions, or alternatively a helical bare region, extending along the active free part. In one embodiment, the free part of the active microcable is provided, except at the distal end, with a stiffener sleeve to vary the stiffness of the assembly along the emerging portion. The stiffener sleeve is preferably a hollow tube composed of helical strands of controlled flexibility, (i.e., a flexibility situated to achieve a desired level or range of flexibility) and partially coated with an insulator material, so as to define a bipolar or multipolar structure. Preferably, the total surface area of the bare region(s) of the free part of the active microcable is at most 40 $mm^2$, more preferably between 4 and 6 $mm^2$.

In a preferred embodiment, the system also includes a radiofrequency puncture generator, which can be connected to the microcable to allow a controlled application at its distal end of a radiofrequency energy sufficient to make a puncture to permit a crossing of the septal wall by the microcable.

In one embodiment, the anchoring means at the distal end of the lead body includes an extending helical screw able to penetrate the wall of the interventricular septum as a result of a screw motion imparted to the lead body at its proximal end. Preferably, the electrode of the lead body coupled to the first terminal of the generator means is a stimulation electrode, placed in the distal region of the lead body. Alternately, it can be a coil forming a right ventricular (RV) defibrillation electrode, designed to be placed in the right ventricle, or a superior vena cava (SVC) defibrillation electrode, designed to be placed in the superior vena cava near the atrium. In one embodiment, the active free part of the microcable includes a distal end portion having a bending stiffness less than the bending stiffness of a less distal adjacent part. Preferably, the active free part is between 5 and 15 mm and is shaped into a flat loop.

As discussed, herein, reference is made to endocardial leads for "stimulation," that is to say for the delivery of low-energy pulses used for bradycardia or resynchronization therapies. But it should be understood that the invention also applies to endocardial leads for delivery of high-energy electric shocks used for cardioversion and/or defibrillation to try to terminate a tachyarrhythmia. Unless otherwise indicated, therefore, the generic terms "stimulation lead (or electrode)" or "stimulation/defibrillation lead (or electrode)" should be understood to refer to any type of lead that can be used for any or all of these purposes.

BRIEF DESCRIPTION OF THE DRAWINGS

Further features, characteristics, and advantages of the present invention will become apparent to a person of ordinary skill in the art from the following detailed description of embodiments of the present invention, made with reference to the annexed drawings, in which:

FIGS. 1-3 illustrate a process for implanting a system for endocardial pacing of the left ventricle in accordance with the present invention;

FIG. 4 is homologous to FIG. 3, for an alternative process for implanting a system for endocardial pacing of the left ventricle in accordance with the present invention;

FIG. 5 is a detailed view of the region crossing the interventricular septum in the final configuration of FIG. 3 or FIG. 4;

FIG. 6 is an enlarged cross-section of the microcable of FIG. 5;

FIG. 7 illustrates an embodiment of a microcable in which the bare region has a helical groove shape; and FIG. 8 illustrates another embodiment of the microcable having a multipolar structure, a variable bending stiffness and a plurality of discrete bare regions.

DETAILED DESCRIPTION

Preferred embodiments of the present invention will now be described with references to the FIGS. 1-8.

In FIG. 1, reference 10 generally designates the heart muscle, showing the right atrium (RA) 12, the right ventricle (RV) 14, the left ventricle (LV) 16 and left atrium (LA) 18. Both ventricles 14 and 16 are separated by the wall or interventricular septum 20, which has a thickness of about 10 to 15 mm. The two atria 12 and 18 are separated by the atrial septum, which has a thickness of 2 to 3 mm.

FIG. 1 illustrates the first step of the intervention, which is to introduce by a conventional approach a screw lead 26 in the right ventricle 14 via the superior vena cava (SVC) 24 and to anchor lead 26 in the wall of the interventricular septum 20.

This lead is, for example, a Stelid BS46D or BeFlex RF46D lead marketed by Sorin CRM, Clamart, France, comprising a lead body of conventional structure with a sheath 28 made of a deformable material, typically a silicone or polyurethane sheath. The lead body is terminated at its distal end, shown in more detail in FIG. 5, by a lead head 30 including a helical screw 32 with non-touching turns having a diameter of, e.g., about 1 to 2 mm. This screw 32 is secured to the lead head 30 by a tip 34 having at its center a lumen and sealing means 36, for example, a silicone perforated cap to prevent any backflow of blood inside the lead body in both the absence and the presence of an element introduced into the lumen of the tip 34 (as in the case shown in FIG. 5).

The lead 26 also carries a distal electrode 38 electrically connected to an inner conductor 40, which is, for example, a coiled conductor extending along the entire length of the sheath 28 to the opposite proximal end of the lead 26. The proximal end is a tip terminated by an electrical connector or plug (not shown) to be coupled to the housing of the implanted generator means, such as a pacemaker/defibrillator or resynchronizer device.

The material and dimensions of sheath 28 may be selected in combination with the spiral conductor 40, to provide some torsional rigidity for the lead body so that it can transmit a torque from the proximal end of the lead 28 (at the electrical connector) to the distal end of the lead head 30. This rotation will allow rotation of the screw 32 for screwing to penetrate into the heart tissue.

The placement of the lead 26 is made according to the following procedure. The first step is to identify an anchoring site by manipulating the lead tip 26 via a conventional stylet introduced into the lumen thereof. The assembly is introduced into the superior vena cava 24, the right atrium 12 and then the ventricle 14 until it abuts against the wall 20 of the interventricular septum.

Once this site is reached, the practitioner transmits an axial rotation movement to the lead body, which has the effect of entering the helical screw 32 in the wall of the interventricular septum 20. The screwing being completed is tactilely detected by the practitioner because of an increase in the resistance to rotation. The axial rotation is transmitted, as appropriate, either directly to the lead body (sheath 28 and spiral conductor 40) or to the connector plug for a pin driven lead (if, at the proximal end, the connector plug is secured to an axial conductor extending within the lead body, this conductor being free in rotation and connected to the helical screw at its distal end).

It should be understood that in the case of a retractable screw (through a conventional and known mechanism), an axial rotation simultaneously deploys the screw out of the slot and ensures its penetration into the myocardial wall.

Alternatively or additionally, if the torsional rigidity of the lead body is not sufficient, it is possible to use in a conventional manner a screw stylet inserted into the inner lumen of the lead 26. The end of the stylet is then coupled to the tip 34 in a conventional manner to rotate the tip, and thus the screw 32, directly from the proximal end of the lead.

The site is then confirmed by radiographic examination at different inclinations. If the position is not satisfactory, the practitioner can unscrew the lead and move it under control to another point and then test the new site.

An implanted screw lead such as the lead 26 as described above is generally used as a detection/stimulation lead after anchoring of the screw at the site of endocardial stimulation. In the case of the present invention, this lead is not only used as a support for at least one sensing/pacing electrode (the distal electrode 38 in the illustrated example), but also as a tool for guiding a microcable through the wall of the septum and beyond it.

As illustrated in FIGS. 2 and 5, the microcable 42 is introduced into the lumen of the sheath 28 of lead body up to the tip 34 and through the silicone perforated cap 36 to abut against the septal wall 20, being oriented substantially in the direction 44 of the central axis of the screw 32.

The practitioner can control the orientation of the axial direction 44 of progression of the microcable 42 by manipulating the curvature of the lead 26 near the region of the anchoring screw 32. Specifically, the orientation of the microcable can be moved to the top of the left ventricle (see arrow 46), by gently pushing the lead 26 so as to accentuate the curvature near the anchoring screw. This is shown in dotted line 48 on FIG. 2. Conversely, a slight pull of the lead will guide the microcable to the apex of the left ventricle 16. The practitioner thus has a significant degree of control over the direction of penetration of the microcable 42 relative to the morphology of the left ventricle 16.

The next step is to puncture or drill a hole in the interventricular septum by using the microcable. This puncture or hole can be achieved by a simple mechanical pushing of the microcable through the interventricular septum, if the microcable rigidity is sufficient.

In a preferred embodiment, forming the hole for passing the microcable is assisted by an RF puncture technique, which is described as follows. After directing the microcable to contact the septal wall 20, the microcable is connected to an RF puncture generator by coupling the output terminal thereof to the electrical connector 52 connected to the proximal end 54 of the microcable 42. (See FIG. 2.) The electrical connector 52 is subsequently connected to the stimulation/defibrillation or resynchronization generator housing in its normal function.

The RF puncture generator 50 is preferably a known model, such as the BMC Radio Frequency Perforation Generator available from Bayliss Medical Company, Inc. This RF puncture generator 50 is used, by coupling to the microcable 42, to operate an "RF puncture" technique of applying a local radio frequency energy produced by an appropriate RF generator to create a very small opening in the septal wall. Such a puncture is generally performed as known in the art by applying low-power RF energy (5-25 W), for a short period of time (1-3 seconds) under a high voltage (150 to 180 V), so as to cause minimal collateral damage to surrounding tissues. This technique of "RF puncture" is distinguished from the "RF ablation" technique, which involves applying a high power (35-50 W) for a more extended period (60 to 90 seconds) under a lower voltage (35 to 50 V). The RF ablation would result, in the application considered here, in creating a larger lesion with thermal destruction of surrounding tissue.

The RF energy produced by the RF puncture generator 50 is applied to the distal end of the microcable 42, which forms a controlled puncture or hole in the interventricular septum 20. The diameter of the hold punctured is essentially defined by the diameter of the microcable 42, for example, in the range of 0.5 to 0.7 mm.

This puncture is obtained by combining, on one hand, the function obtained by the screw lead of guiding the microcable, with, on the other hand, the application of RF energy for the microcable to penetrate the septum. This configuration considerably minimizes the axial force required to be transmitted at the end of the microcable during this step. Indeed, in the absence of applied RF energy, the microcable, if too thin, could not penetrate the tissue and rest at the point of contact with the septum wall. Advantageously, the RF puncture technique also provides cauterization of the traversed tissues as the puncture is formed, and therefore prevents bleeding.

In summary, the lead 28 of the present invention provides for:
Selecting the puncture site on the septum;
Guiding the microcable during the intravenous passage;
Transmitting the pushing force to the tip of the microcable during the puncture;
Stabilizing the microcable during an RF puncture of the septum (if applied);
Defining (orienting) the path of the RF microcable for and during the puncture, with the possibility to test several configurations of implantation; and
Stabilizing and protecting the length of the microcable on the right side of the heart throughout the lifetime of the device.

After the wall 20 has been completely traversed, the RF puncture generator 50 is stopped and disconnected from the microcable 42.

The next step, illustrated in FIGS. 3 and 5, is to push the distal free end portion 58 of microcable 42 beyond the interventricular septum 20, now crossed from one side to the other side, so as to let it emerge in the interior volume of the left ventricle 16, beyond the intermediate part 56 enclosed in the septum 20. The length of free portion 58 can be up to 120 mm, with the example shown in FIG. 3 being a length of about 50 mm.

This free portion 58 of the emerging microcable 42 may be totally or partially bare (a number of embodiments are described below with reference to FIGS. 7 and 8), so as to form an active component, namely a component that is not electrically insulated, which come into contact with one or more points of the interior wall of the left ventricle 16.

The next step is to connect the implanted generator 60 (e.g., pacemaker, defibrillator and/or resynchronizer) to the lead 26 and the microcable 42 so that one terminal of the detection/stimulation circuit of generator 60 is electrically connected to the distal electrode 38 of the lead 26 (i.e., an electrode located in the right ventricle) and the other terminal of that circuit is connected to the free portion 58 of the active microcable 42 (i.e., the component now localized in the left ventricle).

The application of stimulation pulses to these two electrodes produces an electric field, represented by arrows 62 (FIG. 3), including a significant portion of cardiac mass and thus enabling effective stimulation of the left ventricle. It should be understood that the location of the stimulation site seems much less critical with endocardial stimulation than in the case of indirect stimulation via the coronary system. Specifically, even if the stimulation site is less controlled (i.e., the point of contact of the active part of microcable 42 with the wall of the left ventricle 16), one can reasonably expect a quality of stimulation that is at least as high as the best site of indirect stimulation via the coronary system.

Further, it should be understood that according to the present invention, it is possible to introduce via the same lead 26, a plurality of microcables 42, each of which emerges in the left ventricle from the same puncture site.

In one embodiment, where the implanted device is a defibrillator, the free portion 58 of the active microcable 42 is connected to one of the terminals of the shock circuit of the generator 60, and the other terminal of this circuit is connected (with reference to FIG. 3):
To an RV coil 64 disposed in the right ventricle 14, and/or
A SVC coil 66 disposed in the superior vena cava 24 near the right atrium 12; and/or
To the generator housing 60, and/or
To the electrode 38 if it has a sufficient surface area (e.g., approximately 40 mm$^2$).

It should be understood that this configuration advantageously allows coverage of a maximum cardiac mass, despite the relatively small electrode surface compared to a conventional shock electrode. In addition, the application of shock occurs between electrodes located on either side of the septum, the latter being "squeezed" in the electric field: this allows a further increase in the effectiveness of defibrillation, at constant energy, or alternatively to significantly reduce the shock energy and therefore the associated pain, as compared to a conventional shock configuration, wherein the shock would be delivered between the generator housing 60 and the coils 64 and/or 66.

An alternative embodiment, with reference to FIG. 4, illustrates the active portion 58 of the microcable emerging in the left ventricle 16 having a much shorter length (e.g., about 10 mm or less) with a loop shape, so as to press the tip of the microcable against the septum wall of the left ventricle, thereby precisely defining a localized stimulation site. The stimulation remains an endocardial one, but the mobility of the microcable and the surface thereof exposed to the arterial circulation are greatly reduced.

In general, the system in accordance with the present invention provides a number of advantages:
The micropuncture technique reduces the size of the punctured section by about 90% of the puncture size employed in a classical atrial transeptal approach, which implements a lead having a diameter of 5 French inserted into a 7 French catheter;
The size of the puncture and the compact structure of the microcable allow a passage through the interventricular septum—and no longer interatrial—which is located away from the sensitive area of the aortic arch;
The size of the puncture and the compact structure of the microcable allow a passage; passage through the interventricular septum, such that there is no need to cross the mitral valve to stimulate the left ventricle, which compares favorably to a conventional atrial transeptal approach, and preserves the full operation of the mitral valve;
A reduction of approximately 75% of the surface area that is exposed to the arterial circulation, compared to a conventional atrial transeptal approach, with a corresponding reduction of the thromboembolic risk;
A configuration that is compatible with a possible extraction, due to the reduced and constant diameter and a high tensile strength of the microcable (e.g., about 3 kg versus 1 kg for a standard lead);

A simplified method of implantation, requiring only conventional equipment;

Joint stimulation of the septum and of the left ventricle wall by a single lead;

Very low tissue damage—unlike a left endocardial screw lead, which is highly traumatic at the stimulation site;

Simplified management of the risks of air embolism: the microcable emerging in the left ventricle being a massive component and not a hollow catheter, the system is less sensitive to the risk of air embolism.

Examples of different microcable structures suitable for the implementation of the invention are now described, with reference to FIGS. 6-8.

The typical diameter of the internal part of the microcable, that is to say, the not insulated metal part, is about 0.2 to 0.4 mm. The isolation of this part is provided by an insulating polyurethane, silicone, or ETFE, leading to a total diameter of about 0.5 to 0.7 mm for the microcable with its sheath.

These dimensions are to be compared to the diameter of about 0.8 mm for a standard transeptal puncture kit needles (which are used for drilling of the atrial septum with access via the femoral route), and to the 7 French (2.33 mm) or 9 French (3 mm) catheters and to the 5 French (1.66 mm) or 6 French (2 mm) leads used in conventional techniques of catheterization with left endocardial lead in a transeptal approach. The microcable of the invention, even coated with an insulating sheath, is of a much smaller diameter than what is usually used for transeptal procedures.

As the microcable passes through the septum in its middle section 56, it shall withstand the movement of compression in this region, and therefore be especially tough against shear stresses. It must also be highly resistant to bending stresses generated by the movement of the left ventricle, which constrains at each beat the free portion 58 of the active microcable 42.

With reference to FIG. 6, a first example of a microcable structure that meets these different requirements is illustrated, providing also a radio-opacity (for monitoring of the intervention under fluoroscopy) and also sufficient electrical conductivity to ensure delivery of the pacing (stimulation) or defibrillation (shock) pulses with minimum line losses from a Joule effect.

On the structure shown in FIG. 6, the internal part of microcable 42 has a plurality of composite strands 68 twisted together with a central strand surrounded by six peripheral strands. Each composite strand 68 is itself made up of a central core wire 70 in platinum-iridium (for radio-opacity) surrounded by a plurality of composite wires 72 providing the desired mechanical and electrical properties, i.e., six wires 72. Each wire 72 is, for example, made of a silver core (for electrical conductivity) wrapped with nitinol (for the properties of resistance to mechanical stress). These different wires are commercially available, for example, from Fort Wayne Metals Inc. Company, Fort Wayne, USA, and are used in the medical field in particular to manufacture defibrillation conductors.

It should be understood the structure described is exemplary and is in no way exhaustive, and many microcable configurations can be envisaged, for example, "1×3" type structures (e.g., the microcable has a strand of 3 wires), 1×7, 1×19, 7×7 type structures (as in the example shown in FIG. 6, wherein the microcable consists of 7 strands of 7 wires each), 7×19, 19×7, 7×7×7, etc.

The advantages of such a structure lie in the fact that the less mechanically resistant elements (platinum-iridium and silver) are encapsulated either directly in the nitinol sheath (for silver), or at the heart of each strand (for platinum iridium). The consequences of a possible fracture of the strands are thus minimized.

The outer insulation 74 is, e.g., a sheath of polyurethane, silicone, or ETFE, which provides an additional encapsulation of the strand of the microcable.

Portion 58 of the active free microcable is at least partially bare. Preferably, the total area of the bare region(s) of the active free part is between 4 and 6 mm$^2$, this value being of the same order as the active surface of a standard endocardial lead.

Insofar as the free end portion 58 is not anchored to the wall of the left ventricle, the chances of contact of the bare region of the microcable with the target areas of the ventricular wall should be maximized.

One alternative embodiment, illustrated in FIG. 7, is to denude the insulation 74 along a single helical cut 76 on all or part of the length of the active region. The distal end 78 is also left bare, mainly to ensure the output of the RF puncture currents, and it is shaped to remain atraumatic. This solution enables users to "lengthen" the surface of stimulation without increasing the total surface area, and thus increase the probability of contact with the tissues of the left ventricular cavity and in the worst situation, at least a portion of microcable remains in contact with the wall, thus ensuring a maximum distance of a few tenths of a millimeter between the bare region and the tissues to be stimulated.

Alternatively or additionally, the conductive bare regions of the microcable may receive a porous coating, e.g., of TiNi, or be encapsulated by a component uniformly crimped by a swaging technique, which is itself coated in order to improve the electrical performance of the assembly. It is also possible to provide an additional layer formed by a carbon film deposited by sputtering, to improve the biocompatibility between the microcable, its insulation and its environment, in order to prevent degradation of parts in contact with blood flow. U.S. Pat. Nos. 5,370,684 and 5,387,247, both assigned to Sorin Biomedica SpA, describe a suitable method to deposit by sputtering a thin, submicron film of carbon on implantable prostheses such as catheters, heart valves, etc., in polyurethane or silicone. One skilled in the art is referred to these two documents for more details about the technology to make such a carbon deposit.

With reference to FIG. 8, an embodiment of a microcable having a plurality of distinct bare regions 80, 82, successively extending along the active free portion 58, is illustrated in FIG. 8. The microcable 42 is filled within the active portion 58 with the exception of the distal end, with a stiffener sleeve for varying the stiffness of the assembly along the emerging part. The sleeve 82 is for example a HHS tube (trademark) from Fort Wayne Metals Inc., Fort Wayne, USA, which is a hollow tube, composed of helical strands of controlled flexibility designed for this purpose. The sleeve 82 is preferably partially coated with an insulator 84, so as to define a bipolar or multipolar structure (denuded areas 80, 82). This configuration allows a more precise location of the electric field, for example, to ensure during stimulation a faster depolarization wave from the endocardium to the epicardium.

It should be understood that the microcable structure is compact, but not hollow, and is resistant to the compression stresses generated by the contraction of the septum. The stiffer body 86 (at the stiffener sleeve 82) can project the most flexible atraumatic distal tip 88 against the left ventricular free wall, thus ensuring a better contact of the conductive areas of the microcable with tissues.

One skilled in the art will appreciate that the present invention can be practiced by other than the embodiments described herein, which are provided for purposes of illustration and not of limitation.

The invention claimed is:

1. A system for endocardial stimulation/defibrillation of the left ventricle, comprising:

An implantation device housing (60), comprising at least two terminals and a generator means for delivering between the two terminals electrical pulses of stimulation/defibrillation, and An endocardial lead comprising at least one distal stimulation/defibrillation electrode proximally coupled to one of the two terminals, wherein the lead comprises:

A lead body (26) of a deformable material having a distal end and a distal inner open lumen, the distal end (30) for extension into the right ventricle cavity (14), means for anchoring the lead body (32) to an interventricular septum wall (20) of a patient and at least one stimulation/defibrillation electrode (38, 64, 66) proximally coupled to one of the two terminals, and At least one structure adapted to be deployed in the left ventricular cavity, comprising a proximal end, an electrically conductive core (70, 72), an insulating sheath (74) about the core, said structure being slidably housed in the distal inner open lumen of the lead body and extending the entire length of the lead body and including beyond the distal end of the lead body, the length of the structure extendable beyond the distal end of lead body comprising:

an intermediate portion (56), for crossing from one side of the interventricular septum wall (20) to the other side, and an active free portion (58), for emerging into the left ventricle cavity (16), said free portion comprising at least one bare region (76, 80, 82)

wherein said structure is electrically coupled at its proximal end (54) to the other of the two terminals of the generator means for producing, upon activation of the generator means, an electric field (62) between said at least one stimulation/defibrillation electrode (38, 64, 66) of the lead body and said at least one bare region (76, 80, 82) of the active free portion (58) of said structure, wherein said structure extendable into the left ventricle cavity comprises a microcable (42) having an electrically conductive core diameter in the active free portion of between 0.2 and 0.4 mm, and comprises a strand formed of a plurality of strands with at least one composite strand (68) comprising:

A first material having properties of mechanical resistance to bending fatigue superior than those of other materials of the strand, and A second material that is radio-opaque.

2. The system of claim 1, wherein the length of the active free portion (58) is between 30 and 120 mm.

3. The system of claim 2 wherein the length of the active free portion is between 45 and 55 mm.

4. The system of claim 1, wherein the length of the intermediate portion (56) is between 10 and 20 mm.

5. The system of claim 1, wherein the diameter of the insulating sheath of the microcable is between 0.5 and 0.7 mm.

6. The system of claim 1, wherein said at least one composite strand (68) further comprises:

A third material having properties of electrical conductivity greater than those of the other materials of the strand.

7. The system of claim 1, wherein the microcable strand is formed of a plurality of composite strands (68), with a core wire (70) comprising said second material, this core wire being surrounded by composite wires (72) each including said first material as a surface material.

8. The system of claim 1, wherein the active free portion (58) of the microcable includes a plurality of distinct bare regions (80, 82) extending in succession along the active free portion.

9. The system of claim 1, wherein the active free portion (58) of the microcable is provided, with the exception of the distal end, with a stiffener sleeve (82) for varying the stiffness of the structure emerging free portion.

10. The system of claim 9, wherein the sleeve stiffener (82) comprises a hollow tube formed of helical strands of a selected flexibility and partially coated with an insulator (84), so as to define a bipolar or multipolar structure.

11. The system of claim 1, wherein the active free portion (58) of the microcable comprises a helical bare region (76) extending along the active free portion.

12. The system of claim 1, wherein the total surface of the bare regions (76, 80, 82) of the active free portion (58) of the microcable is less than about 40 mm$^2$.

13. The system of claim 12 wherein the total surface area of the bare region is between 4 and 6 mm$^2$.

14. The system of claim 1, further comprising: A radiofrequency puncture generator (50), connected to the microcable for a controlled application at the distal end a radiofrequency energy sufficient to achieve a crossing of the septum wall by said microcable.

15. The system of claim 1, wherein the means for anchoring the distal end of the lead body comprises an extending helical screw (32) for penetration into the interventricular septum wall (20) under the effect of a screw motion imparted to the lead body (26) from the proximal end thereof.

16. The system of claim 1, wherein said electrode of the lead body coupled to said first terminal of the generator means is a stimulation electrode (38), arranged in the distal region of the lead body.

17. The system of claim 1, wherein the electrode of the lead body coupled to said first terminal of the generator means are of a coil forming an RV defibrillation electrode (64, 66), for implantation in the right ventricle and an SVC defibrillation electrode, for implantation in the superior vena cava near the atrium.

18. The system of claim 1, wherein the active free portion of the microcable comprises a distal end part (88) having a bending stiffness less than that of a less distal adjacent part (86).

19. The system of claim 1, wherein the active free portion has a length of between 5 and 15 mm and is shaped into a loop.

* * * * *